United States Patent
Sarrafzadeh et al.

(10) Patent No.: US 8,845,554 B2
(45) Date of Patent: Sep. 30, 2014

(54) METHOD AND APPARATUS FOR QUANTITATIVE ASSESSMENT OF NEUROMOTOR DISORDERS

(75) Inventors: Majid Sarrafzadeh, Anaheim Hills, CA (US); Roozbeh Jafari, Los Angeles, CA (US); Victor R. Edgerton, Los Angeles, CA (US); Devin L. Jindrich, West Hollywood, CA (US); Foad Dabiri, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 708 days.

(21) Appl. No.: 12/528,777

(22) PCT Filed: Mar. 7, 2008

(86) PCT No.: PCT/US2008/056271
§ 371 (c)(1), (2), (4) Date: Aug. 26, 2009

(87) PCT Pub. No.: WO2008/112567
PCT Pub. Date: Sep. 18, 2008

(65) Prior Publication Data
US 2010/0113979 A1 May 6, 2010

Related U.S. Application Data

(60) Provisional application No. 60/906,083, filed on Mar. 9, 2007.

(51) Int. Cl.
*A61B 5/103* (2006.01)
*A61B 5/11* (2006.01)
(Continued)

(52) U.S. Cl.
CPC ............ *A61B 5/1107* (2013.01); *A61B 5/0002* (2013.01); *A61B 2562/043* (2013.01); *A61B 5/6825* (2013.01); *A61B 5/225* (2013.01)
USPC ........................................ 600/587; 600/595

(58) Field of Classification Search
USPC ......... 600/300, 301, 304, 546, 547, 551, 552, 600/553, 561, 587–595
See application file for complete search history.

(56) References Cited

U.S. PATENT DOCUMENTS 5,643,138 A * 7/1997 Huang .............................. 482/4
6,872,187 B1 * 3/2005 Stark et al. ..................... 602/16
(Continued)

OTHER PUBLICATIONS

Jafari et al., "CMAS: Clinical Movement Assessment System for Neuromotor Disorders" Biomedical Circuits and Systems Conference, 2006, BioCAS 2006, IEEE, pp. 102-105.
(Continued)

*Primary Examiner* — Max Hindenburg
*Assistant Examiner* — Renee Danega
(74) *Attorney, Agent, or Firm* — Foley & Lardner LLP; Cliff Z. Liu; Angela D. Murch

(57) ABSTRACT

The present invention relates to methods and apparatus for quantitative assessment of neuromotor disorders using sensors and analyzing the data collected from the sensors to determine if a patient suffers any neuromotor disorders. In one embodiment, the present invention is a system for assessing neuromotor disorders in a body including a plurality of pressure sensors adapted for attachment to the body and measuring pressure, a med node connected to the plurality of pressure sensors for generating data corresponding to the plurality of pressure sensors, and an analysis unit connected to the med node for analyzing the data generated by the med node to determine the existence of a neuromotor disorder in the body.

14 Claims, 8 Drawing Sheets

(51) Int. Cl.
 *A61B 5/00* (2006.01)
 *A61B 5/22* (2006.01)

(56) References Cited

U.S. PATENT DOCUMENTS

2005/0113652 A1* 5/2005 Stark et al. .................... 600/300
2006/0195018 A1* 8/2006 Guillen ......................... 600/300

OTHER PUBLICATIONS

Chui et al., "Assessment of cerebral autoregulation using time-domain cross-correlation analysis", Computers in Biology and Medicine, vol. 31, Mar. 26, 2001, pp. 471-480.

Dumont et al., "Dynamic force-sharing in multi-digit task", Clinical Biomechanics, vol. 21, 2006, pp. 138-146.

* cited by examiner

| TASK | SUBJECT | VARIANCE IN ERRORS WITH RESPECT TO THE TARGET FORCE (%) | | | | | FREQUENCY DIFFERENCE (Hz) | | | | |
|---|---|---|---|---|---|---|---|---|---|---|---|
| | | AVERAGE | LITTLE FINGER | RING FINGER | MIDDLE FINGER | INDEX FINGER | AVERAGE | LITTLE FINGER | RING FINGER | MIDDLE FINGER | INDEX FINGER |
| 1 | 1 | 5.56 | 88.18 | 46.00 | 23.51 | 90.80 | 0.002 | -0.085 | 0.000 | 0.002 | 0.001 |
| 1 | 2 | 7.34 | 77.40 | 30.58 | 57.48 | 99.26 | 0.002 | 0.003 | 0.002 | 0.003 | -0.052 |
| 2 | 1 | 0.78 | 89.40 | 10.82 | 66.63 | 99.78 | 0.000 | -0.023 | -0.008 | -0.002 | -0.044 |
| 2 | 2 | 1.06 | 72.51 | 21.22 | 67.61 | 100.00 | 0.000 | -0.025 | 0.000 | -0.011 | -0.049 |
| 3 | 1 | 61.15 | 93.55 | 44.39 | 54.84 | 98.34 | 0.360 | -0.368 | 0.356 | 0.361 | -0.037 |
| 3 | 2 | 15.89 | 78.44 | 33.18 | 55.23 | 100.00 | 0.003 | -0.204 | 0.003 | 0.002 | -0.683 |
| 4 | 1 | 0.44 | 88.74 | 32.95 | 40.56 | 86.11 | -0.001 | -0.022 | -0.031 | -0.022 | -0.029 |
| 4 | 2 | 0.15 | 77.29 | 29.64 | 40.44 | 98.48 | 0.001 | -0.035 | -0.015 | -0.010 | -0.023 |

FIG. 10

METHOD AND APPARATUS FOR QUANTITATIVE ASSESSMENT OF NEUROMOTOR DISORDERS

This application claims the benefit of U.S. Provisional Patent Application No. 60/906,083 filed on Mar. 9, 2007, entitled "METHOD FOR QUANTITATIVE ASSESSMENT OF NEUROMOTOR DISORDERS" which is expressly incorporated herein in its entirety.

BACKGROUND OF THE INVENTION

1. Field of the Invention

The present invention relates to a method and apparatus for quantitative assessment of neuromotor disorders collecting data from sensors and analyzing the data collected from the sensors to determine if a patient suffers any neuromotor disorders.

2. Description of Related Art

Recently, health care costs have increased at a rapid rate with much of the costs tied to the care and diagnosis of patients. The diagnosis of a patient can be costly since it may be hard for a human physician to quantitatively gauge what is wrong with a patient. Without a correct diagnosis, the physician may not administer the correct care for a patient. In addition, early stages of a disease or disability may not be readily apparent to a physician. These problems can be especially apparent with respect to neuromotor disorders since the type and severity of the neuromotor disorder may be concealed and/or hard to quantify.

BRIEF SUMMARY OF THE INVENTION

The present invention seeks to solve problems described above by providing a method and apparatus for quantitative assessment of neuromotor disorders.

In one embodiment, the present invention is a system for assessing neuromotor disorders in a human body a plurality of pressure sensors to the body to measuring by attaching pressure exerted, a med node connected to the plurality of pressure sensors for generating data corresponding to the pressure sensors, and an analysis unit connected to the med node for analyzing the data generated by the med node to determine the existence of a neuromotor disorder in the body.

BRIEF DESCRIPTION OF THE DRAWINGS

The exact nature of this invention, as well as the objects and advantages thereof, will become readily apparent from consideration of the following specification in conjunction with the accompanying drawings in which like reference numerals designate like parts throughout the figures thereof and wherein:

FIG. 10 is a chart of results from a preliminary experiment using the present invention;

DETAILED DESCRIPTION OF THE INVENTION

Figure 1:
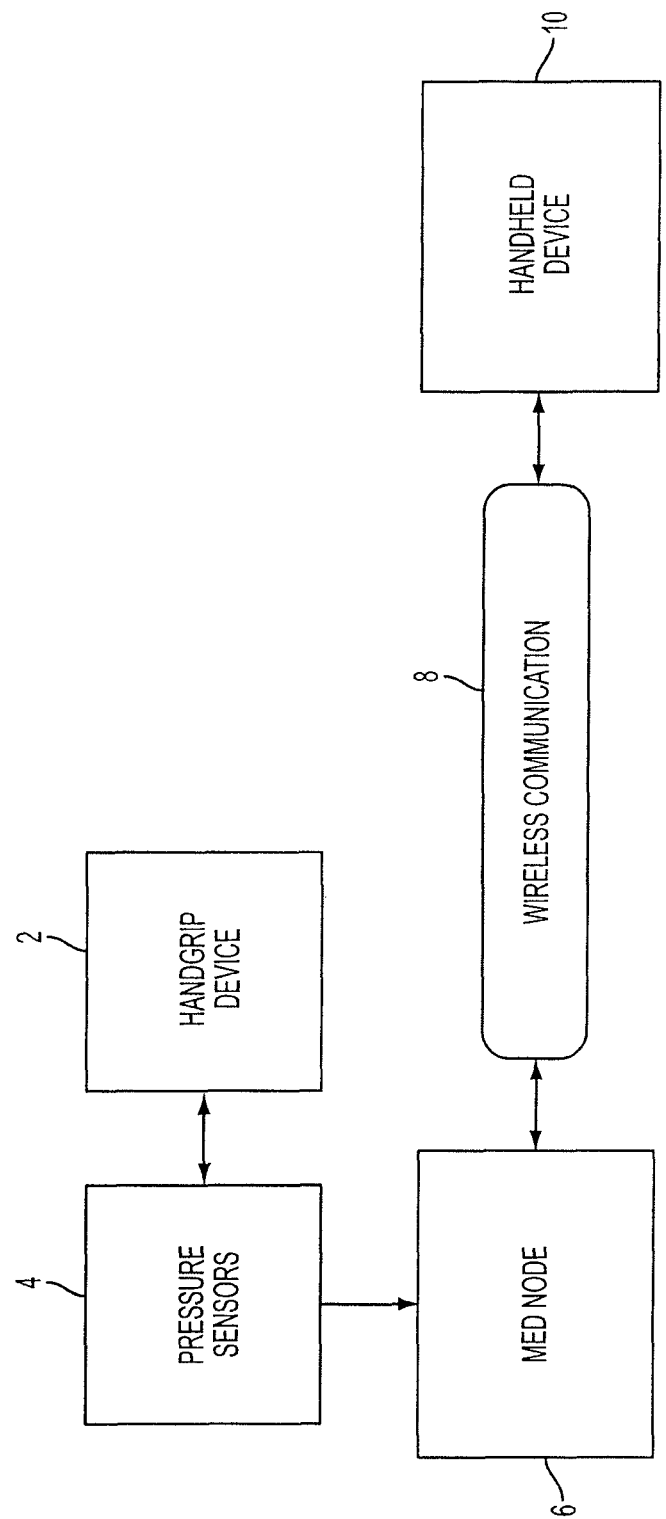
FIG. 1 is a block diagram of the present invention.

FIG. 1 is a block diagram illustrating an embodiment of the present invention. As shown in FIG. 1, a system for assessing neuromotor disorders in a body includes a handgrip device 2, pressure sensors 4 connected to the hand grips for measuring pressure executed, a med node 6 for collating data from the pressure sensors, and, wireless communication link 8, connecting the med node 6 to an analysis unit 10.

Handgrip device 2 (FIG. 2) has pressure sensors 4 to measure pressure exerted by the individual fingers on the handgrip 2. The pressure exerted could be from each finger of a hand, or any other portion of the hand. Pressure sensors 4 are used to measure both static and dynamic force and can be thin enough to enable non-intrusive measurement which is ideal for measuring forces without disturbing the dynamics of a test. Other sensors that can be used aside from pressure sensors 4 include, but are not limited to, sensors that detect galvanic skin response, flex sensors, piezoelectric film sensors, and temperature sensors.

Figure 2:
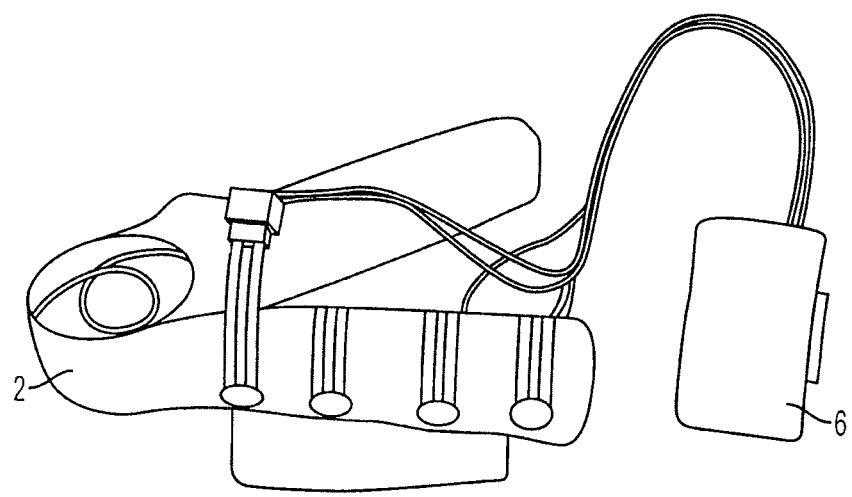
FIG. 2 is a perspective view of a handgrip device attached to a med node as used in the present invention.

Med node 6 is connected to the pressure sensors 4, to gather information from the Sensors 4 and generate data corresponding to the pressure sensed by the plurality of pressure sensors. It is preferred that med node 6 be connected directly to handgrip device 2, as shown in FIG. 2. Med node 6 is customizable to suit a range of applications, such as tracking knee motion after knee surgery or aiding Alzheimer patients residing in assisted living homes by detecting arousal and/or agitation by measuring skin conductance. Med node 6 may also support a variety of analog and digital sensors.

Med node 6 is software programmable to suit various applications and sensors. On-chip memory blocks are used within med node 6 for data storage. Med node 6 generates data in response to the pressure sensors 4 on the handgrip device 2.

Analysis unit 10 which may be a handheld device is connected to med node 6 for analyzing the data generated by med node 6 for the purpose of determining the existence of a neuromotor disorder. As a handheld unit, analysis unit 10 may be a pocket PC, a mobile phone, a smart phone, or an iPod®, or similar functioning mobile device. When analysis unit 10 is a handheld device, it is connected to the med node 6 by wireless communication link 8. Wireless communication link 8 may be a radio wave link, Bluetooth® link, a cellular communication link, for example or any similar functioning communication link. Although a wireless communication link 8 is illustrated in FIG. 1, any communication link may be used, including wired communication links.

Analysis unit 10 collects the data from med node 6 and classifies the collected data. Analysis unit 10 also coordinates and controls the overall functionality of the system including handgrip 2, pressure sensors 4, and med node 6. Analysis unit 10 may also performs resource management to accommodate several objectives such as optimizing the power or enhancing the fault-tolerance. Analysis unit 10 is capable of communicating with other electronic devices such as a PC or the Internet. Analysis unit 10 may also be adapted to interact with patients.

Figure 3:
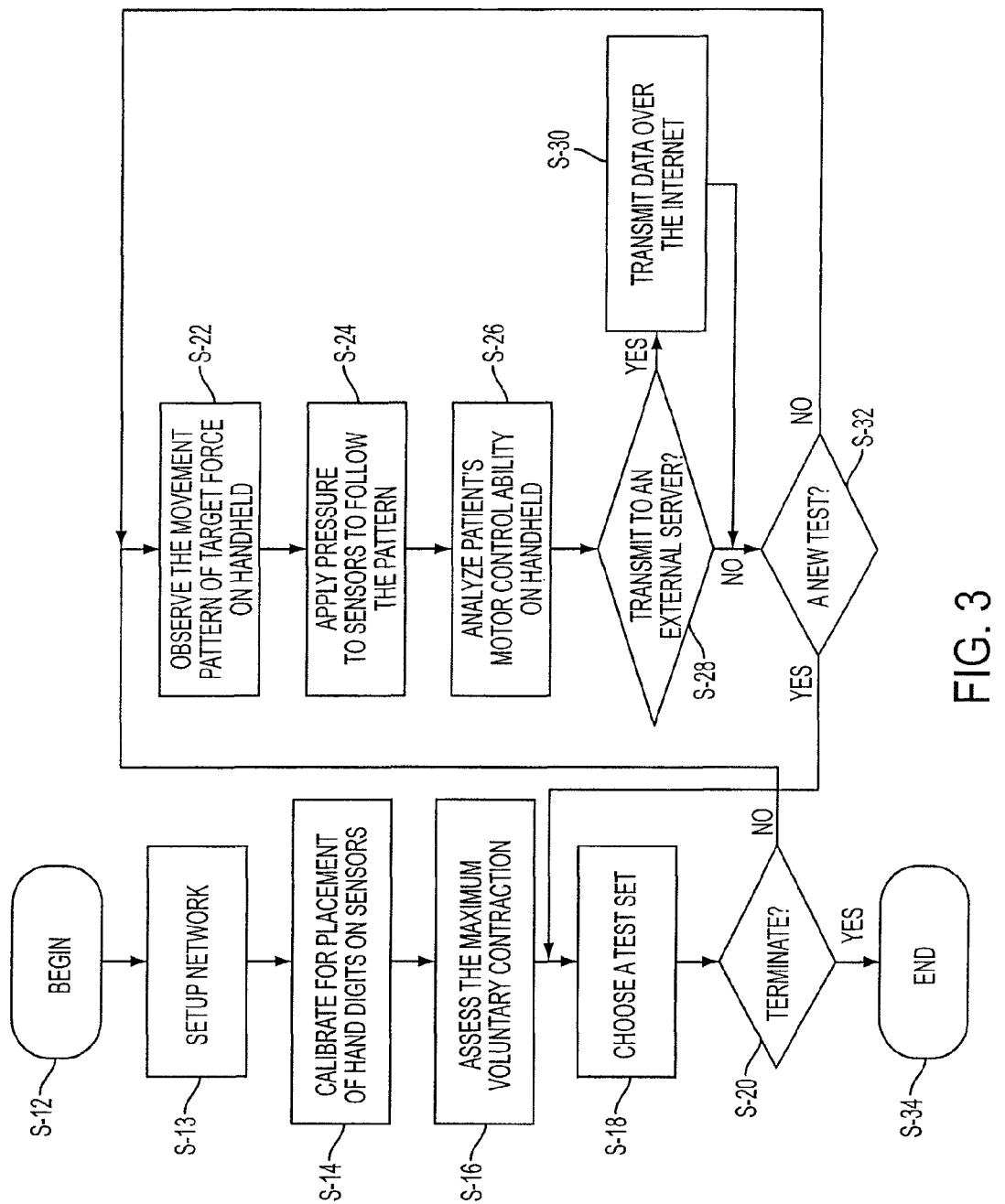
FIG. 3 is a flowchart of the test procedure of the present invention.
Figure 4:
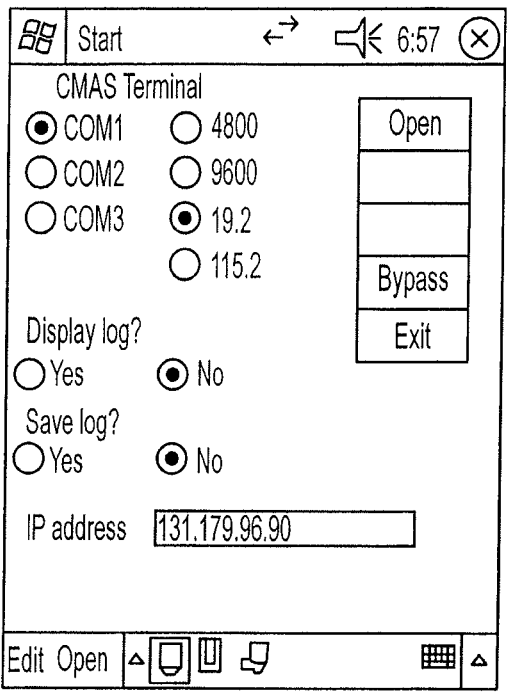
FIG. 4 is an example of a screen for network setup on a handheld device as used in the present invention.

FIG. 3 is a flowchart of a process of the present invention to detect neuromotor disorders. The process begins at step S-12 with a start signal. At step S-13, the network is set up by an operator, as shown in FIG. 4. The network can be set up by a doctor, nurse, a hospital staff, or a user.

Figure 5:
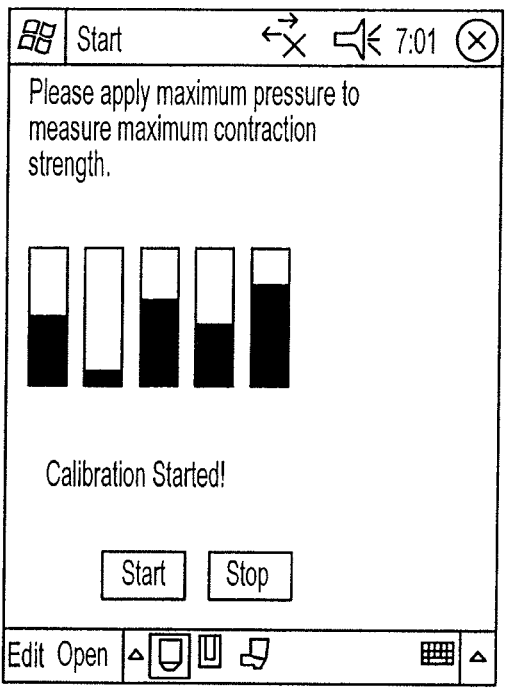
FIG. 5 is an example of a screen for maximum voluntary contraction on a handheld device as used in the present invention.

In step S-14, pressure sensors 4 on handgrip 2 are calibrated. After gripping the handgrip 2, the user exerts the maximum pressure he can by squeezing the hand grip. The maximum voluntary contraction of the user's hand at step S-16 as seen in FIG. 5, calibrates the system.

Figure 6:
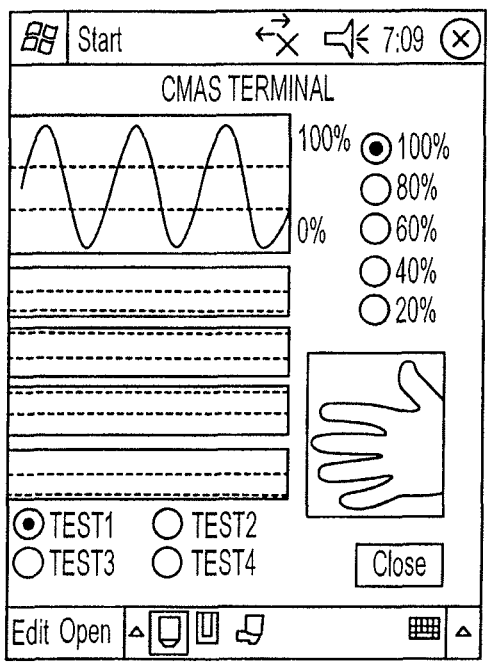
FIG. 6 is an example of a screen for a test set on a handheld device as used in the present invention.

At step S-18, the user or diagnostician chooses a test set that the user should be capable of performing as seen in FIG. 6. At step S-20 an analysis is performed to see if the process should be terminated. The process will be terminated when the user becomes tired, or if a predetermined condition has been met, or if further tests would be detrimental to the user. If the decision is made not to terminate the process, the process proceeds to step S-22.

At step S-22, the user observes a pattern of a target force on analysis unit 10. The user then applies pressure to pressure sensors 4 on handgrip 2 following the pattern of the target force, in step S-24. Using the results of the applied pressure, analysis unit 10 analyzes the user's motor control ability, in step S-26.

Analysis unit 10 determines if the data and analysis should be transmitted to an external server in step S-28. If the data and/or analysis should be transmitted, analysis unit 10 transmits the relevant information over a communication link, such as the Internet for example, in step S-30. However, if data and/or analysis transfer is inappropriate, analysis unit 10 determines if the user wants to perform a new test in step S-32. The user will be allowed to choose a new test at step S-18.

If the user does not want to perform a new test, but would rather to repeat the same test, steps S-22 through S-28 can be repeated. If the user does not want to repeat the test, then step S-18 is repeated until the user wants to terminate. The user can terminate at step S-20. The process ends at step S-34.

To analyze the patient's motor control ability, analysis unit 10 may perform frequency matching, time-domain cross-correlation, variance measure, and/or force sharing with respect to the relevant data collected by the analysis unit 10. This analysis can not only measure the ability of fingers to track a pre-established face pattern, but also the ability to determine how the individual fingers coordinate amongst themselves.

Frequency matching is accomplished by using a Discrete Fourier Transform (DFT). More specifically, the DFT can be used to calculate the power spectrum of the monitored signal, and determine the frequency at peak power (FPP).

The DFT, X, of a signal x can be expressed by the equation:

$$X(k) = \sum_{j=1}^{N} x(j)\omega_N^{(j-1)(k-1)}$$

where $$\omega_N = e^{\frac{(-2\pi i)}{N}}$$

The power as a function of frequency can be calculated as:

$$P = X^2$$

Figure 7:
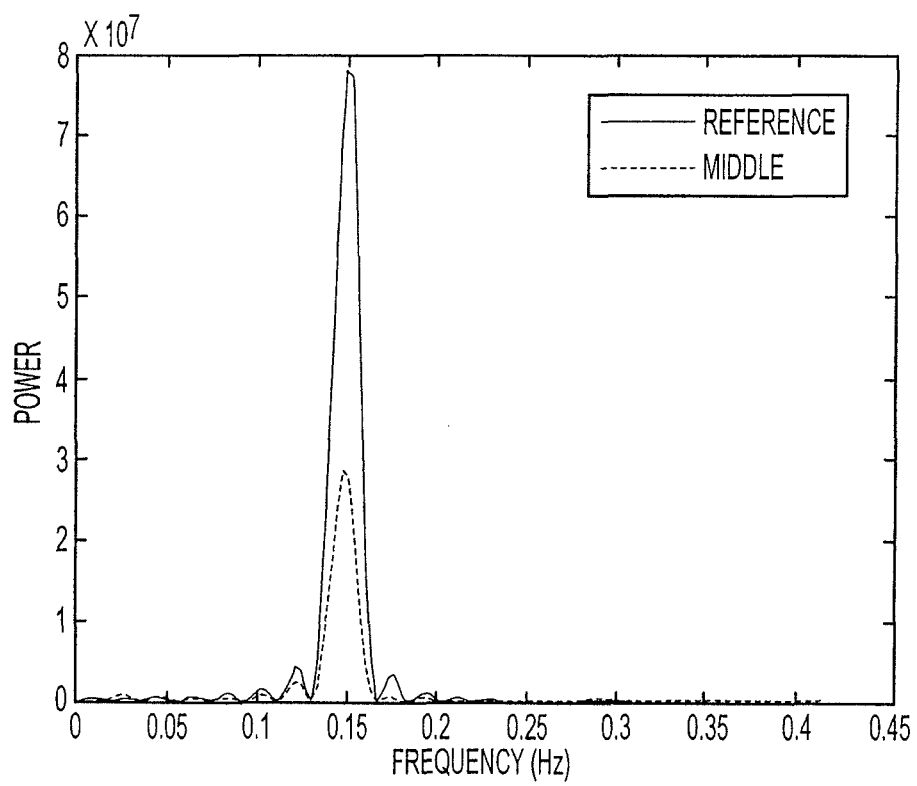
FIG. 7 is a graph showing an example of frequency matching as used in the present invention.

For the timed series, the FFP from each of the force sensors, is determined. The difference between a reference FPP and the finger FPP is calculated as shown in FIG. 7. Frequency matching yields a measure of the degree to which the frequency of force generation by individual fingers matches the target frequency as provided by a reference.

Figure 8:
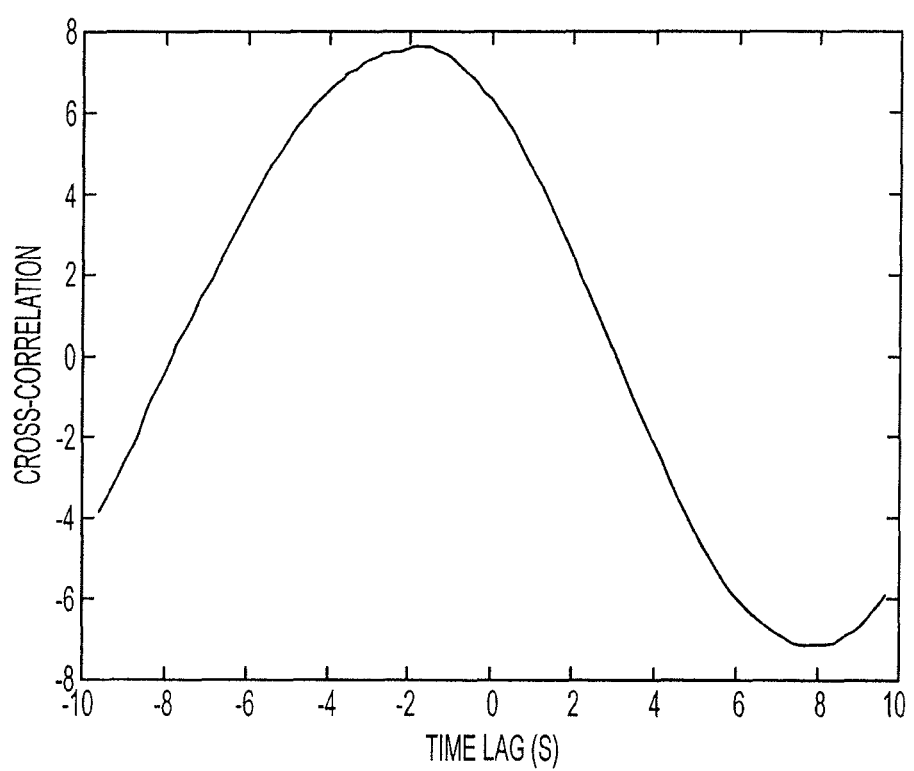
FIG. 8 is a graph showing an example of cross-correlation.

The ability of individual fingers, and the entire hand, to effectively track a reference signal in time can be calculated using the cross-correlation function. The cross-correlation is a measure of similarity between two signals, and can also be used to determine the relative time lag between the two signals. The cross-correlation can be calculated as:

$$R_{xy}(m) = \frac{\sum_{n=0}^{N-m-1} x_{n+m} y_n}{N - |m|}$$

Where x and y are time series of length N, and m ranges from −N to N (or a specified shorter interval). The time lag (m) corresponding to the peak of the cross-correlation function can be used as an indicator of the time lag between the two signals, even if the signals are complex as shown in FIG. 8.

In addition to measuring the ability of fingers to track a reference face pattern, cross-correlation can also be used to measure the ability of the individual fingers to coordinate amongst themselves. To measure the amount of coordination between fingers using cross-correlation, the force time series from individual fingers are used as inputs (x and y) to the cross-correlation function. Peak cross-correlations and time lags at peak correlations can be measured for comparisons between fingers.

To calculate the error between the reference (target) force (R) and the force generated by an individual finger or the entire hand (F), the "variance accounted for" (VAF) can be calculated using the following equation:

$$VAF = 100 * \left[ 1 - \frac{\sum_{t=0}^{t=\tau}[R(t) - F(t)]^2}{\sum_{t=0}^{t=\tau} R(t)^2} \right]$$

The VAF can express the tracking error of a given finger, or the hand, normalized to the variance of a reference signal. It is contemplated that normal healthy people are able to track the target free patterns well. This could lead to VAF values close to 100% for normal people. On the other hand, impairments on a test patient leads to a decrease in performance in tracking targets. This in turn leads to a decrease in the VAF. Healthy people could have a VAF close to 100% while impaired people will have a VAF<100% (i.e. 20%, 50%, etc.)

The force sharing ability (FS) of the fingers can be calculated using the following equation:

$$FS = \frac{\sum \text{Var}F_i(t) - \text{Var}F_{tot}(t)}{\sum \text{Var}F_i(t)}$$

Where $\text{VarF}_i(t)$ can be the variance in force (across cycles or trials) of the target force for an individual finger i at cycle timepoint t. $\text{VarF}_{tot}(t)$ can be the variance (across cycles or trials) in the summed force produced by all the fingers at cycle timepoint t.

If FS is positive, then negative co-variation among finger forces can indicate extensive force sharing among the fingers. If FS is smaller or negative, then force sharing among the fingers can be reduced. Healthy people are expected to have high, positive values of FS (i.e. 0.9-1), FS will decrease with disease or injury.

Figure 9:
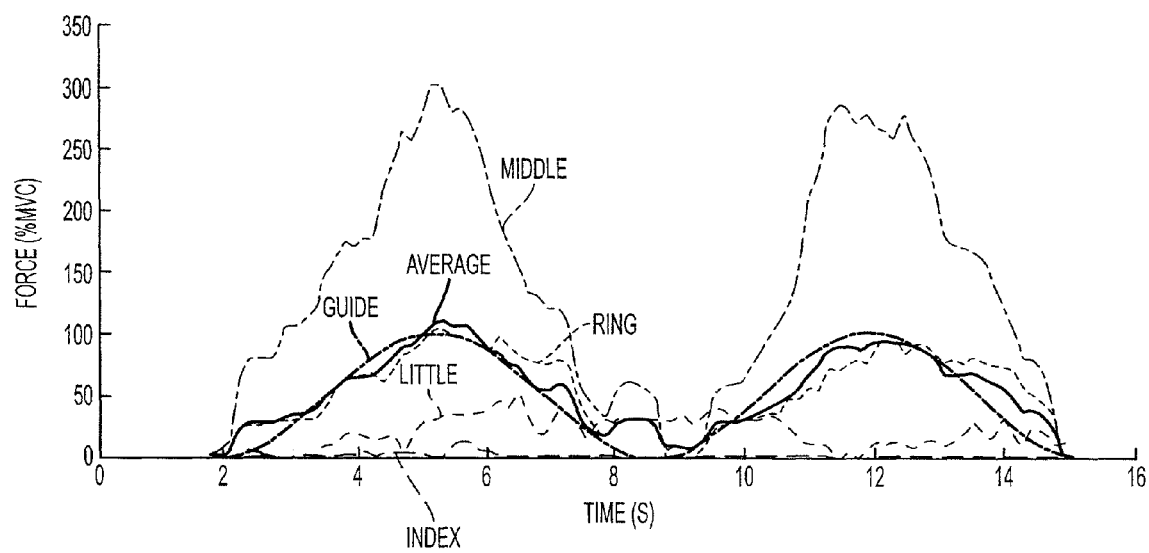
FIG. 9 is a graph showing results from a preliminary experiment using the present invention.

Preliminary experiments conducted on unimpaired subjects (N=2) showed that healthy subjects were able to finely modulate finger forces to achieve a desired average force as shown in FIG. 9. These experiments involved four test sets:

Test 1: The guide or the target travels on a sinusoidal waveform between 0 and 100% of the patient's maximum strength. The period of the sine wave could be 6 seconds.

Test 2: This test can be used to evaluate the fatigability in a patient. The target moves between 20% and 40% of the maximum voluntary contraction (MVC) with a period of 200 ms. The patient is expected to follow the indicator by rapidly squeezing the handgrip device.

Test 3: This test can be used to evaluate the patient's ability to finely modulate force production. The guide moves between 15% and 30% of the MVC on a sinusoidal wave with a period of 6 seconds.

Test 4: This test can be used to test the high strength fine grain motor control. This test can be similar to test 3 except that the guide moves between 45% and 65% of the MVC.

The variance in errors between average force and target forces were 6.4 f 1.0%, 0.9±5%, 38 f 0.3% and 0.3 f 0.3% of the guide variance for Task 1, 2, 3 and 4, respectively for the healthy subjects over 6 trials. Subjects precisely matched the guide frequency (frequency differences <0.005 Hz for all trials). Cross-correlating the guide signal with the average force signal revealed that average forces from subjects lagged the guide forces by 80 f 100 ms and 300±0 ms for tasks 2 and 3. For tasks 1 and 4, the time mean time lags of −50 ms and −21 ms fell well within the variance 170 and 470 ms, respectively.

Whereas subjects were able to precisely track the guide signals, they did not accomplish this by generating comparable forces with each finger as shown in FIG. 9. Large forces produced by middle fingers compensated for small forces generated by index and little fingers, reflecting an effective force synergy that maintained target average forces. The variance in errors between each individual force and the target forces is shown for every task and subject in FIG. 10. In addition, in the frequency domain, the difference of the peak in the power spectrum between each individual force and the target forces is shown. Please note that each data point in FIG. 10 is the average taken over 3 trials.

Obviously many modifications and variations of the present invention are possible in light of the above teachings. It is therefore to be understood that within the scope of the appended claims the invention may be practiced otherwise than as specifically described.

We claim:

1. A system for assessing neuromotor disorders in a body, comprising:
    a hand-held device containing a plurality of pressure sensors for measuring pressure applied by the individual fingers of a hand of a person holding the device;
    a med node connected to the plurality of pressure sensors for generating data corresponding to signals generated by the pressure sensors;
    a screen display of a target force pattern for observation by the person holding the device for the purpose of the person holding the device tracking the displayed target force pattern with the individual fingers of the hand holding the device, while the target force pattern is being displayed; and
    an analysis unit connected to the med node for analyzing the data generated by the med node to determine the existence of a neuromotor disorder in the body;
    wherein the analysis unit is configured to analyze the data generated by the med node using time-domain cross-correlation to measure the similarity between the force pattern generated by the individual fingers of the hand and the target force pattern.

2. The system of claim 1 wherein the analysis unit is configured to analyze the data generated by the med node using frequency matching to determine the degree to which the frequency of force generated by the individual fingers matches the frequency of force of the target force pattern.

3. The system of claim 1 wherein the analysis unit is configured to analyze the data generated by the med node using variance calculations to calculate the difference between the target force pattern and the force pattern generated by the fingers.

4. The system of claim 1 wherein the analysis unit is configured to analyze the data generated by the med node using force sharing calculations to calculate the variance between applied force over time by an individual finger, or all the fingers, and the target force pattern.

5. The system of claim 1 wherein the analysis unit is sized to be held by one hand of the person.

6. A method for determining abnormal pressure patterns applied by fingers on a hand of a person holding a sensor device containing sensors for each of the fingers, the method comprising:
    receiving signals corresponding to a force pattern applied by the fingers to the sensor; and
    analyzing the signals produced by the sensors, to determine the existence of a neuromotor disorder;
    wherein analyzing the signals from the sensors includes using time-domain cross-correlation to measure the similarity between the force pattern generated by the individual fingers and the target force pattern.

7. The method of claim 6 wherein analyzing the signals from the sensor device includes using frequency matching to determine the degree to which the frequency of force generated by the individual fingers matches the frequency of force of the target force pattern.

8. The method of claim 6 wherein analyzing the signals from the sensor device includes using variance calculations to calculate the difference between the target force pattern and the force pattern generated by the fingers.

9. The method of claim 6 wherein analyzing the signals from the sensor device includes using force sharing calculations to calculate the variance between applied force over time by an individual finger, or all the fingers, and the target force pattern.

10. The system of claim 1 wherein the target force pattern being displayed for observation by the person holding the device is a predetermined pattern, a random pattern, or an adaptive pattern based on the person's ability to track the observed pattern.

11. The method of claim 6 further comprising calibrating the sensor device by applying the maximum pressure exertable by the person on the device.

12. A method, comprising:
    presenting on a display screen a pattern of a target force representing a target sequence of force to be applied to a plurality of pressure sensors of a handgrip;
    receiving data from the plurality of pressure sensors indicating at least one actual sequence of force applied to the plurality of pressure sensors in response to the presenting the pattern of the target force on the display screen; and
    cross-correlating the target sequence and the actual sequence in the time domain, thereby identifying a time lag between the sequences.

13. The method of claim 12, wherein the time lag indicates an ability to follow the pattern of the target force.

14. The method of claim 12, further comprising cross-correlating two actual sequences in the time domain, thereby identifying a time lag between the sequences, wherein a first of the two actual sequences is a sequence of data from a first one of the plurality of pressure sensors, and a second of the two actual sequences is a sequence of data from a second one of the plurality of pressure sensors, wherein the time lag indicates an ability to coordinate motion of two fingers placed on the handgrip.

\* \* \* \* \*